(12) United States Patent
Sanchez et al.

(10) Patent No.: US 11,931,257 B2
(45) Date of Patent: Mar. 19, 2024

(54) DEVICES AND METHODS FOR AORTIC VALVE PREPARATION PRIOR TO TRANSCATHETER PROSTHETIC VALVE PROCEDURES

(71) Applicant: Medtronic, Inc., Minneapolis, MN (US)

(72) Inventors: Jorge Zhingre Sanchez, Minneapolis, MN (US); Anthony Nesberg, Minneapolis, MN (US); Erik Jagger, Minneapolis, MN (US); Jeffrey Sandstrom, Minneapolis, MN (US); Vijayanarayan Madhavan Potti, Minneapolis, MN (US); Jacob McHenry, Minneapolis, MN (US); Michael Bateman, Minneapolis, MN (US); Ryan Stublaski, Minneapolis, MN (US); Ana Menk, Minneapolis, MN (US); Paul Rothstein, Minneapolis, MN (US); Joel Racchini, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 676 days.

(21) Appl. No.: 16/364,488

(22) Filed: Mar. 26, 2019

(65) Prior Publication Data

US 2019/0298517 A1 Oct. 3, 2019

Related U.S. Application Data

(60) Provisional application No. 62/648,669, filed on Mar. 27, 2018.

(51) Int. Cl.
*A61F 2/24* (2006.01)
*A61B 17/3205* (2006.01)
(Continued)

(52) U.S. Cl.
CPC ...... *A61F 2/2427* (2013.01); *A61B 17/32053* (2013.01); *A61B 17/3207* (2013.01);
(Continued)

(58) Field of Classification Search
CPC ........ A61F 2/2427; A61F 2/24; A61F 2/2418; A61B 17/3207; A61B 17/32053;
(Continued)

(56) References Cited

U.S. PATENT DOCUMENTS 6,047,700 A 4/2000 Eggers et al.
6,071,277 A 6/2000 Farley et al.
(Continued)

OTHER PUBLICATIONS

D. Dvir, "Transcatheter Laceration of Aortic Leaflets to Prevent Coronary Obstruction During TAVR—Concept to First-in-Human BASILICA Procedures", Cardiovascular Research Foundation, tct2017, Sep. 19, 2018, pp. 1-51.
(Continued)

*Primary Examiner* — Linda C Dvorak
*Assistant Examiner* — Bradford C. Blaise
(74) *Attorney, Agent, or Firm* — Wentsler LLC

(57) ABSTRACT

Aspects of the disclosure relate to devices and methods for preparing an existing, implanted prosthetic aortic valve for subsequent prosthetic aortic valve implantation. To prepare the existing valve, a valve preparation device is delivered to the valve and valve leaflets are severed either via mechanical cutting or electrodes so that the leaflets cannot obstruct a blood flow path once a prosthetic valve is subsequently implanted within the valve. Similarly, in alternate embodiments, devices and methods of the disclosure can be used for preparing a native aortic valve for delivery and implantation of a prosthetic valve.

17 Claims, 15 Drawing Sheets

(51) Int. Cl.
  *A61B 17/3207* (2006.01)
  *A61B 18/00* (2006.01)
  *A61B 18/14* (2006.01)
  *A61B 17/00* (2006.01)
  *A61B 17/22* (2006.01)
  *A61B 17/32* (2006.01)

(52) U.S. Cl.
  CPC ........ *A61B 18/1492* (2013.01); *A61F 2/2418* (2013.01); *A61B 2017/00867* (2013.01); *A61B 2017/22061* (2013.01); *A61B 2017/22097* (2013.01); *A61B 17/320016* (2013.01); *A61B 2017/32006* (2013.01); *A61B 2018/00369* (2013.01); *A61B 2018/00601* (2013.01); *A61B 2018/1407* (2013.01); *A61B 2018/1422* (2013.01); *A61B 2018/144* (2013.01); *A61B 2018/1475* (2013.01)

(58) Field of Classification Search
  CPC ........ A61B 18/1492; A61B 17/320016; A61B 2017/22097; A61B 2018/1422; A61B 2017/32006; A61B 2017/22061; A61B 2017/00867; A61B 2018/00369; A61B 2018/00601; A61B 2018/1407; A61B 2018/144; A61B 2018/1475; A61B 2018/00214; A61B 2018/00267
  USPC .......................................................... 606/46
  See application file for complete search history.

(56) References Cited

U.S. PATENT DOCUMENTS

| | | |
|---|---|---|
| 6,142,994 A | 11/2000 | Swanson et al. |
| 8,808,237 B2 | 8/2014 | Thielen et al. |
| 2002/0173811 A1 | 11/2002 | Tu et al. |
| 2003/0212394 A1* | 11/2003 | Pearson ............. A61B 18/1477 606/41 |
| 2006/0271081 A1 | 11/2006 | Realyvasquez |
| 2007/0083194 A1* | 4/2007 | Kunis ................ A61B 18/1492 606/41 |
| 2007/0185513 A1 | 8/2007 | Woolfson et al. |
| 2007/0239154 A1* | 10/2007 | Shaolian ............ A61F 2/2445 623/2.37 |
| 2008/0188880 A1 | 8/2008 | Fischer et al. |
| 2009/0149848 A1* | 6/2009 | Werneth ............... A61B 18/18 606/33 |
| 2009/0209955 A1 | 8/2009 | Forster et al. |
| 2013/0116715 A1 | 5/2013 | Weber |
| 2013/0150881 A1 | 6/2013 | Wang et al. |
| 2014/0012257 A1 | 1/2014 | Epp et al. |
| 2014/0128949 A1* | 5/2014 | Hollett ................ A61N 1/0519 607/116 |
| 2015/0011991 A1* | 1/2015 | Buysman ........... A61B 18/1492 606/41 |
| 2015/0088246 A1 | 3/2015 | Astarci et al. |
| 2015/0238218 A1 | 8/2015 | Morales et al. |
| 2016/0100855 A1 | 4/2016 | LeMaitre et al. |
| 2016/0183877 A1* | 6/2016 | Williams .............. A61B 5/287 606/41 |
| 2017/0014183 A1 | 1/2017 | Gifford, III et al. |
| 2017/0105762 A1 | 4/2017 | Bloom et al. |
| 2017/0150984 A1 | 6/2017 | Breen |
| 2018/0028258 A1 | 2/2018 | Zamarripa et al. |
| 2018/0325456 A1* | 11/2018 | Klebanov ........... A61B 5/6885 |
| 2019/0069949 A1* | 3/2019 | Vrba .................... A61B 18/02 |

OTHER PUBLICATIONS

M. Kleman et al., "How to perform combined cutting balloon and high pressure balloon valvuloplasty for dogs with subaortic stenosis", Journal of Veterinary Cardiology (2012) 14, 351-361.

International Search Report and the Written Opinion for International Application No. PCT/US2019/024080 dated Aug. 21, 2019. (17 pages).

Office action from counterpart European Patent Application No. 19716697.8 dated Aug. 30, 2022.

* cited by examiner

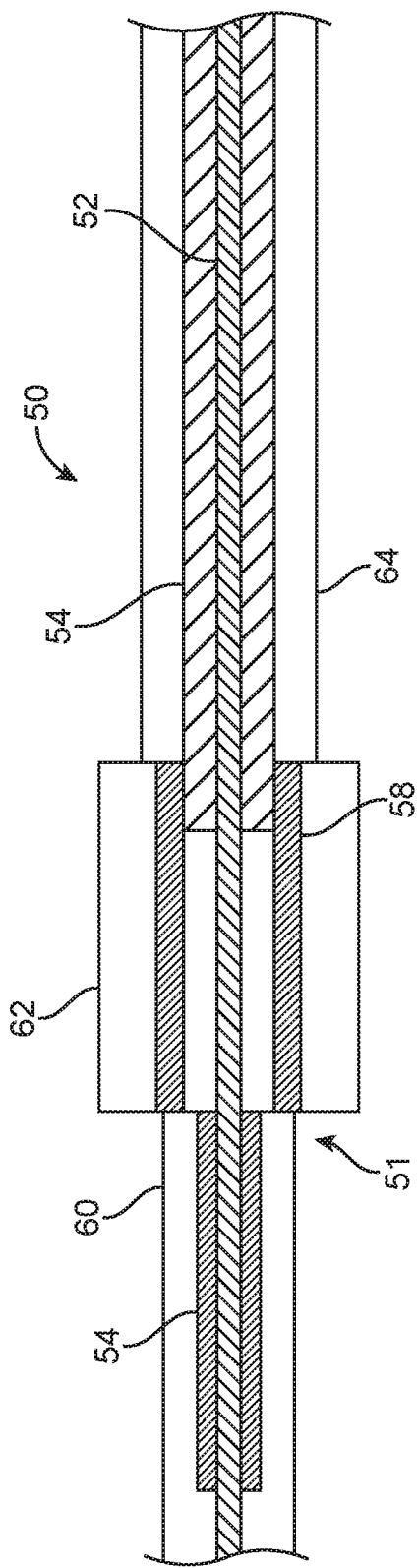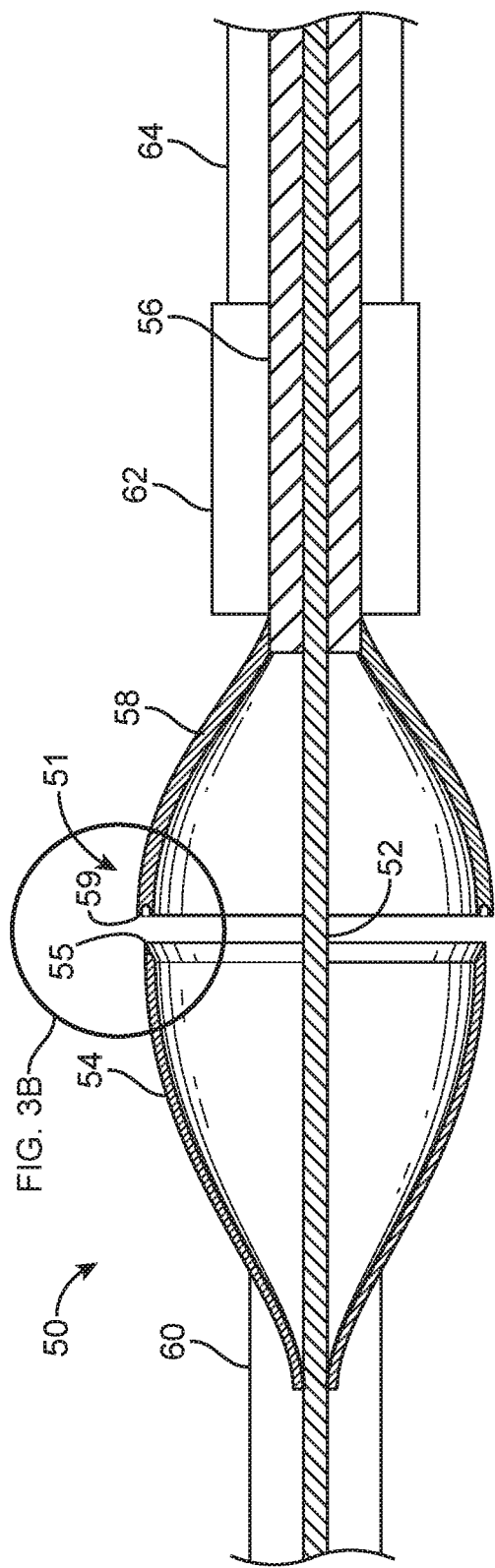

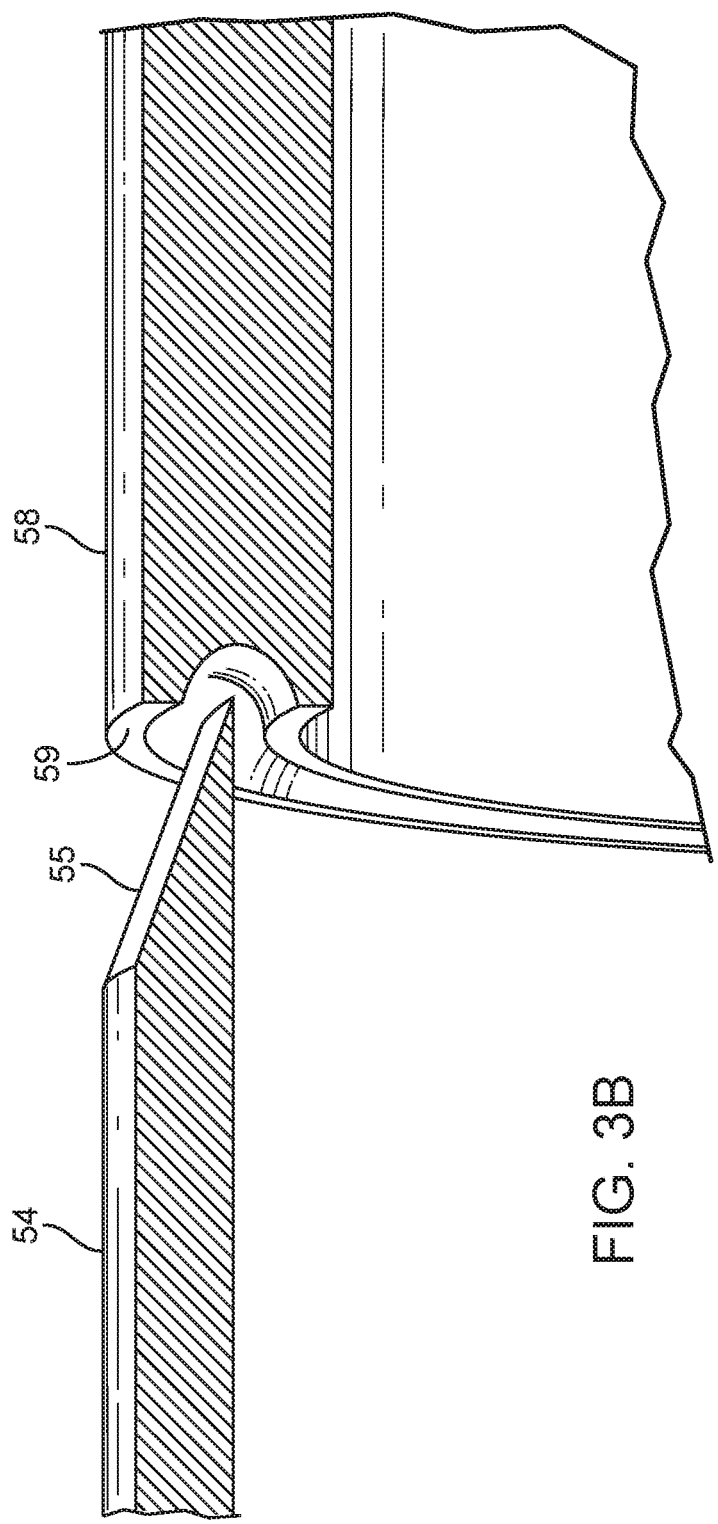

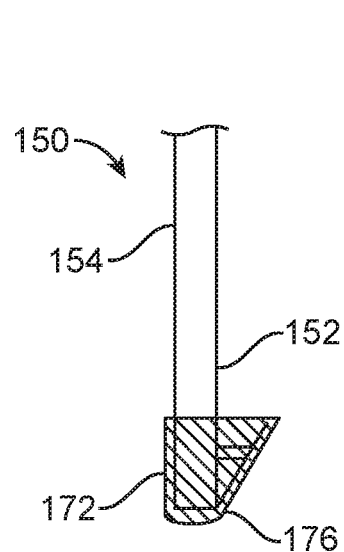
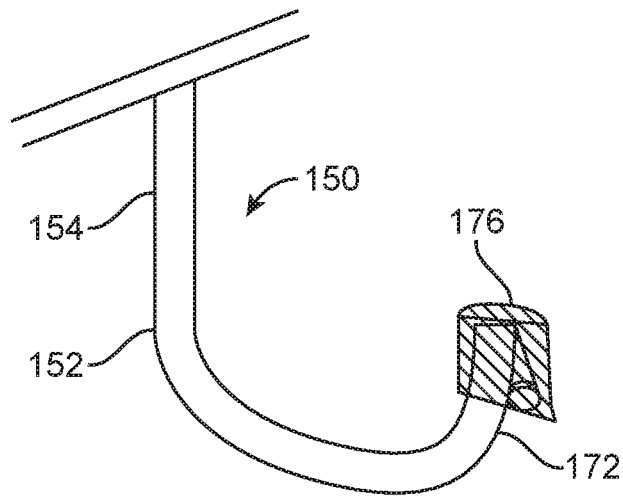
FIG. 8A  FIG. 8B
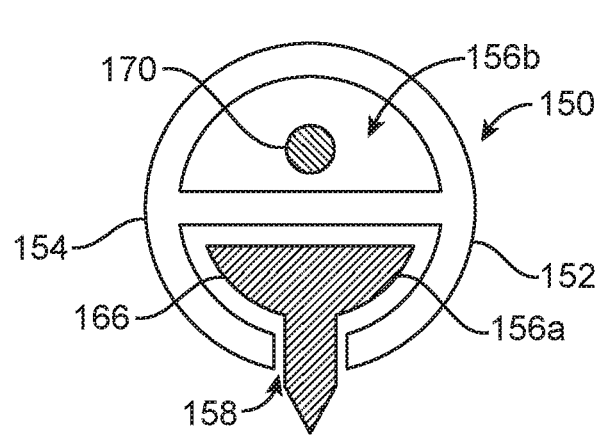
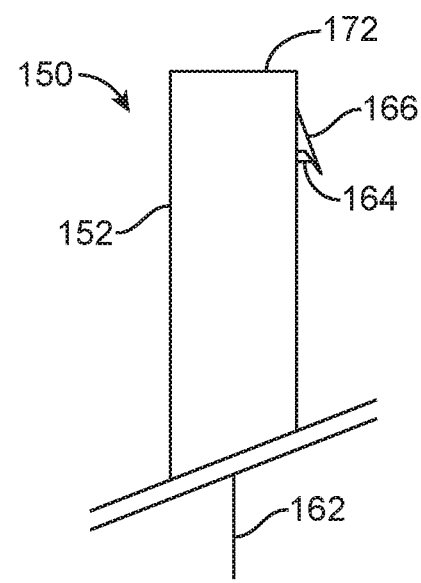
FIG. 9  FIG. 10

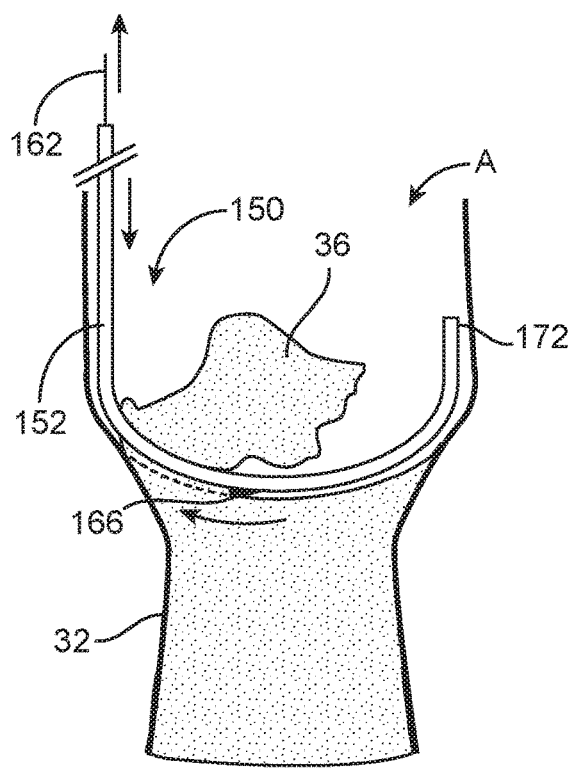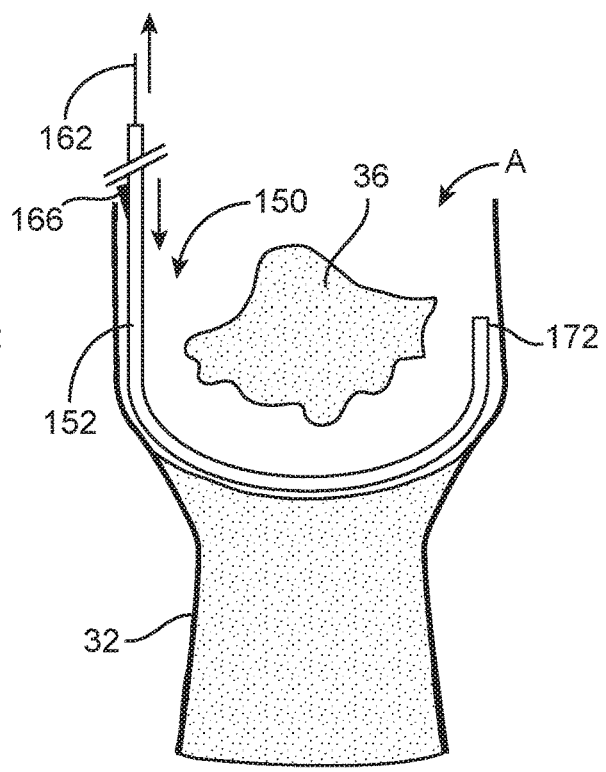
FIG. 12F  FIG. 12G
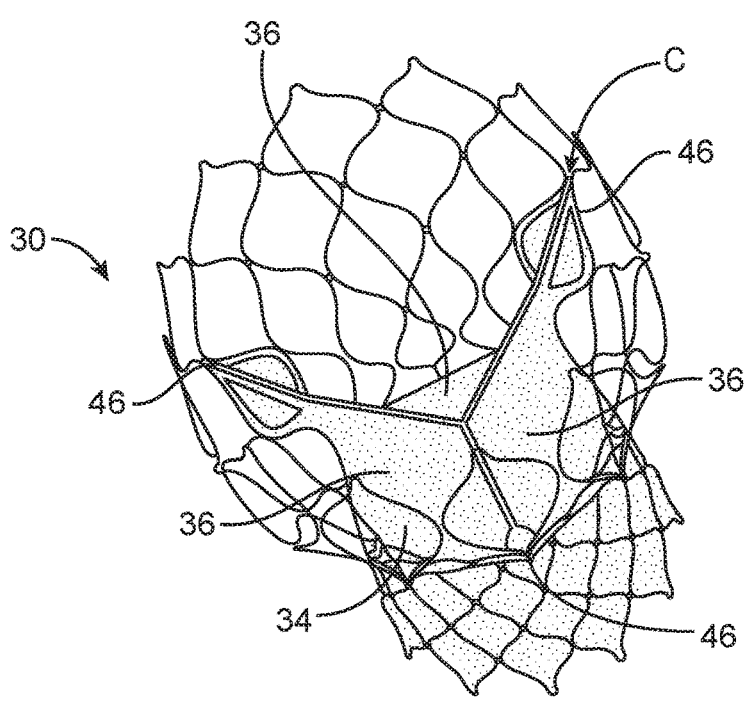
FIG. 13

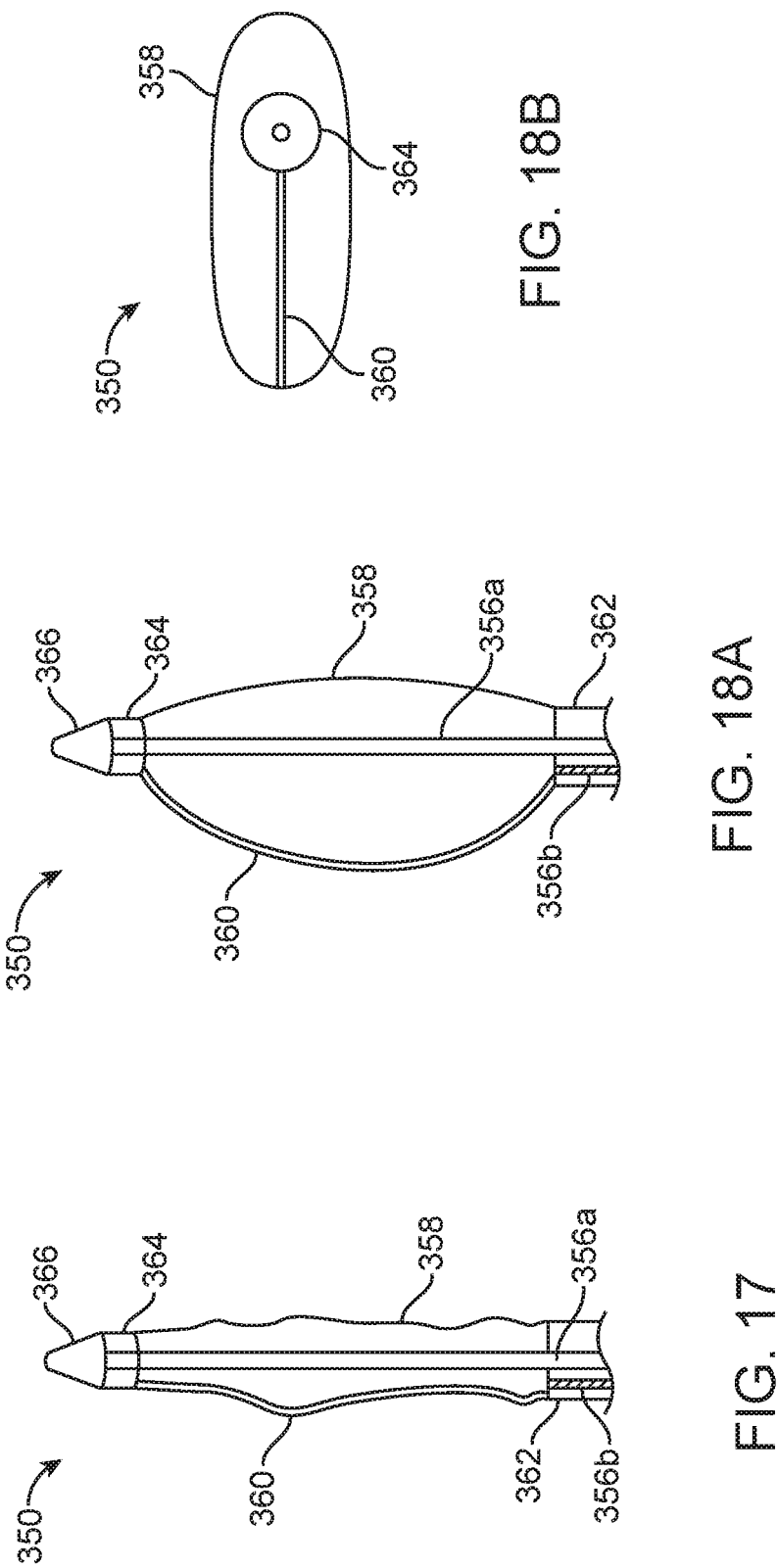

DEVICES AND METHODS FOR AORTIC VALVE PREPARATION PRIOR TO TRANSCATHETER PROSTHETIC VALVE PROCEDURES

CROSS-REFERENCE TO RELATED APPLICATIONS

This Non-Provisional Patent Application claims the benefit of the filing date of U.S. Provisional Patent Application Ser. No. 62/648,669, filed Mar. 27, 2018, the entire teachings of which are incorporated herein by reference.

BACKGROUND

Aortic stenosis is a degenerative heart valve disease that is treated with surgical aortic valve (SAV) and transcatheter aortic valve (TAV) replacement bioprostheses having tissue leaflets that often will eventually fail. The treatment of failing bioprosthetic valves with repeat replacement bioprosthesis implantation procedures may present complications, including coronary artery obstruction risks and future percutaneous coronary intervention difficulties.

The present disclosure addresses problems and limitations with respect to the above.

SUMMARY

Aspects of the disclosure relate to devices and methods for preparing an existing, implanted transcatheter prosthetic aortic valve for subsequent transcatheter prosthetic aortic valve implantation. Such devices and methods mitigate coronary artery obstruction risks from repeat valve replacement procedures while additionally facilitating future access for percutaneous coronary intervention. Alternatively, it is also envisioned that devices and methods of the disclosure can be used in preparing a native aortic valve for delivery and implantation of a prosthetic valve.

Various methods of preparing an aortic valve for implantation of a prosthetic aortic valve comprise the steps of providing a patient having an aortic valve (either prosthetic or native) including at least one leaflet, providing a valve preparation device including a severing apparatus and delivering the severing apparatus to the aortic valve with the valve preparation device via transcatheter delivery. Then, the severing apparatus is engaged with at least one leaflet to sever the leaflet(s) and optionally release the leaflet(s) from a remainder of the aortic valve. If necessary, the valve preparation device is then moved to another leaflet and the other leaflet is detached or slit. The process could optionally continue until more or all leaflets are detached from the stent frame. Once severed, the leaflets may be removed via an embolic protection device, for example. The valve preparation device is withdrawn from the patient and the valve is ready for implantation of a prosthetic heart valve. It is noted that if the leaflets are removed or significantly altered, the patient may require a temporary valve to provide hemodynamic stability until the new valve is implanted. It is understood that any of the concepts discussed could be used in conjunction with a temporary valve (such as within the ascending or descending aorta). In some embodiments, the temporary valve could also be incorporated onto the delivery catheter(s).

Various valve preparation devices are disclosed. Disclosed embodiments generally include a valve preparation device for severing heart valve leaflets, the valve preparation device comprising a first catheter and a severing apparatus configured to sever calcified heart valve leaflets.

One valve preparation device includes a first portion connected to a first catheter and a second portion connected to a second catheter that is coaxially aligned with the first catheter. The first portion and the second portion are each made of a memory shape material that is biased to bow outwardly with respect to central axis of the device. In a delivery position, one capsule contains a first portion of a severing system and a second capsule contains a second portion of the severing system. Once delivered and in position, the first and second portions are unsheathed so that the first and second portions expand to their natural, bowed position. Then, the first and second catheters are arranged so that the first and second portions engage each other on opposing sides of a valve leaflet or otherwise contact opposing sides of the valve leaflet. Either via engagement of the first and second portions or contact via electrodes, the first and second portions collectively sever the leaflet.

Yet another disclosed valve preparation device includes a catheter having a body defining a first lumen and a second lumen. The catheter further defining a track extending through the body from the second lumen. An articulation apparatus provided within the first lumen that can be actuated to articulate the body to deliver a severing apparatus, provided in the second lumen, to a leaflet. The severing apparatus can include a hook and a blade or an electrode that at least partially extends within the track for cutting a leaflet once positioned adjacent thereto.

In a further embodiment, a valve preparation device includes a severing apparatus including a wire and at least one arm that is biased to bow outwardly with respect to the wire. Each arm further includes an electrode that can be actuated to cut the leaflet. A tip is connected to a distal end of the wire for puncturing the leaflet to position each arm electrode adjacent the leaflet. The device further includes a sheath movable from a delivery position in which the sheath covers the severing apparatus and a deployed position in which the sheath is proximally retracted to uncover the severing apparatus.

In a further embodiment, a valve preparation device includes a severing apparatus including a balloon and at least one wire that carries energy to sever the leaflet. The balloon is inflated to preferentially push the energized wire from the base of the leaflet to the free edge of the leaflet. A tip is connected to a distal end of the device for puncturing the leaflet to position the balloon and wire in the appropriate location.

Methods of preparing an aortic valve for implantation of a prosthetic aortic valve are also enclosed. Various methods include providing a patient having an aortic valve including a first leaflet and providing a valve preparation device including a severing apparatus. The severing apparatus is delivered to the aortic valve with the valve preparation device via transcatheter delivery. Then, the severing apparatus is engaged with the first leaflet and the first leaflet is severed. Then, the valve preparation device from the patient. In some embodiments, one or more leaflets are also removed from the patient.

BRIEF DESCRIPTION OF THE DRAWINGS

FIG. 2 is a partial, cross-sectional, schematic illustration of a valve preparation device including first and second portions that interconnected to respective catheters and are compressed by respective distal and proximal capsules.

FIG. 3A is a partial, cross-sectional, schematic illustration of the valve preparation device of FIG. 2 illustrating the capsules moved to unsheathe the respective portions and allow the portions to self-expand.

FIG. 3B is a partial, enlarged, schematic illustration of the valve preparation device of FIG. 3A.

FIG. 8A is a partial, schematic illustration of a valve preparation device in a straight configuration.

FIG. 8B is a partial, schematic illustration of the valve preparation device of FIG. 8A in an articulated configuration.

FIG. 9 is a cross-sectional illustration of the valve preparation device of FIGS. 8A-8B.

FIGS. 10-11B are partial, schematic illustrations of the valve preparation device of FIGS. 8A-9.

FIGS. 12A-12G are partial, schematic illustrations of the valve preparation device of FIGS. 8A-11B as the valve preparation device is positioned adjacent one leaflet of a previously implanted prosthetic valve to remove the leaflet from a remainder of a prosthetic valve (wherein a portion of the stent frame is removed for ease of illustration).

FIG. 13 is a perspective view of the prosthetic valve of FIGS. 1A-1B indicating, via a bold arrow, where a distal end of the device is to be positioned during the step as illustrated in FIG. 12C.

FIG. 17 is a partial, schematic illustration of an alternate valve preparation device utilizing a balloon (shown as transparent for ease of illustration); wherein the balloon is in a deflated or delivery arrangement.

FIG. 18A is a partial, schematic illustration of the valve preparation device of FIG. 17, the balloon (shown as transparent for ease of illustration) being in a deployed, inflated arrangement.

FIG. 18B is an end view of the of the valve preparation device of FIG. 18A, the balloon (shown as transparent for ease of illustration) being in the deployed, inflated arrangement.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein, with reference to an implanted stented prosthesis, the term "outflow" is understood to mean downstream to the direction of blood flow, and the term "inflow" is understood to mean upstream to the direction of blood flow.

Figure 1A:
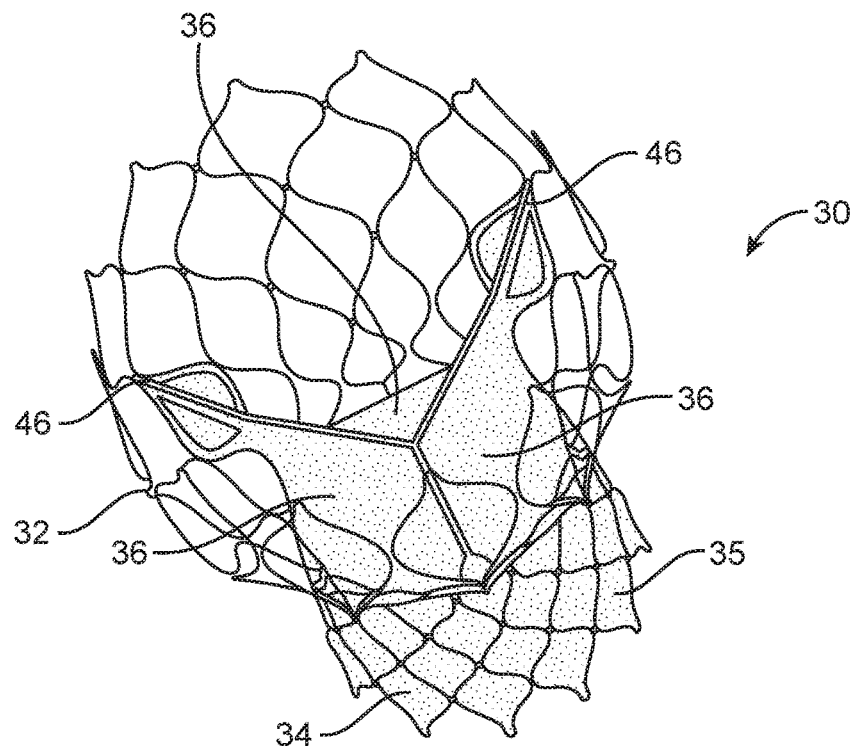
FIGS. 1A-1B are views of one suitable prosthetic valve that can be used with the devices and methods of the disclosure.
Figure 1B:
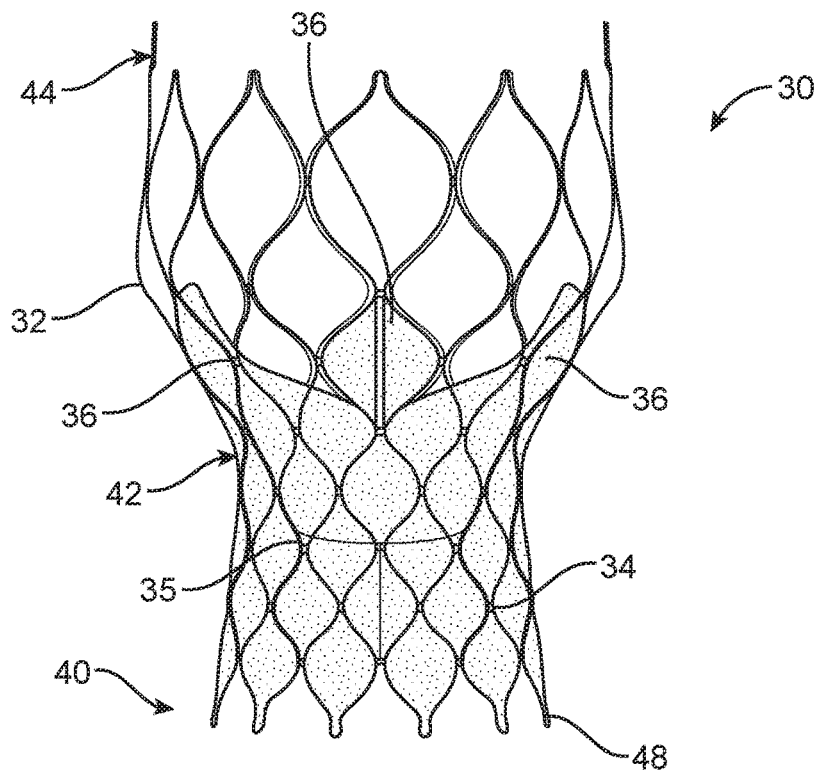

By way of background, one non-limiting example of a prosthetic heart valve 30 that may be implanted at an aortic valve is illustrated in detail in FIGS. 1A-1B. As a point of reference, the prosthetic heart valve 30 is shown in a normal or expanded arrangement in the views of FIGS. 1A-1B. The prosthetic heart valve 30 includes a stent or stent frame 32 and a valve structure 34. The stent frame 32 can assume a variety of forms and is constructed to be self-expandable from the compressed arrangement to the normal, expanded arrangement. Other frames may be constructed to be expandable via balloon or surgically implanted, for example.

The valve structure 34 of the stented prosthesis 30 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 is formed from heart valve tissue, pericardium, and/or other suitable tissue. The valve structure 34 can include or form one or more leaflets 36. For example, the valve structure 34 can be in the form of a tri-leaflet bovine pericardium valve, a bi-leaflet valve, or another suitable valve.

In some prosthetic valve constructions, such as that of FIGS. 1A-1B, the valve structure 34 can comprise two or three leaflets 36 that are fastened together at enlarged lateral end regions to form commissural joints 46, with the unattached edges forming coaptation edges of the valve structure 34. The leaflets 36 can be fastened to an optional skirt 35 that in turn is attached to the stent frame 32. The stented prosthesis 30 includes a first end 40 (inflow), an opposing second end 44 (outflow) and an intermediate section or waist 42. As shown, the stent frame 32 can have a lattice or cell-like structure, and optionally forms or provides posts (not shown) corresponding with commissures 46 of the valve structure 34 as well as features 48 (e.g., crowns, eyelets or other shapes) at either or both of the first and second ends 40, 44. If provided, the commissure joints 46 are spaced equally around frame 32.

Over time, the leaflets 36 can fail or otherwise function inadequately, thus requiring replacement. Treating failing prosthetic heart valves with repeat replacement procedures in which a replacement prosthetic heart valve is positioned within the previously implanted prosthetic heart valve may present complications, including coronary artery obstruction risks and future percutaneous coronary intervention difficulties due to blood flow blockages caused by the leaflets of the previously implanted prosthetic heart valve. The present inventors have discovered devices and methods of transcatheter aortic valve replacement of a previously implanted transcatheter aortic valve that reduce the aforementioned risks. With such devices and in such procedures, leaflets of the previously implanted transcatheter aortic valve are removed/modified so that the previously implanted leaflets do not occlude or block access to the coronaries.

One embodiment of a valve preparation device 50 is schematically illustrated in FIGS. 2-7. FIG. 2 illustrates the valve preparation device 50 having a severing system 51, both shown in a delivery configuration. The valve preparation device 50 includes an inner catheter 52 extending a length of the device 50. Attached to the inner catheter 52 is a first portion 54 of the severing system 51. In some embodiments, proximal/distal movement of the inner catheter 52 correspondingly moves the first portion 54. The device 50 further includes a middle catheter 56 positioned over and coaxially aligned with the inner catheter 52. A second portion 58 of the severing system 51 is secured to the middle catheter 56 and proximal/distal movement of the middle catheter 56 can be transferred to correspondingly move the second portion 58 along the inner catheter 52. The device 50 further includes first and second capsules 60, 62, each covering one of the first and second portions 54, 58 in the delivery configuration. For example, the first capsule 60 can be positioned over the inner catheter 52 and can compressively retain and sheathe the first portion 54 in the delivery configuration. As shown, the second capsule 62 is connected to an outer shaft 64 that is coaxially aligned with the inner and middle catheters 52, 56 and can be moved distally and proximally to correspondingly control movement of the second capsule 62.

FIG. 3A illustrates the valve preparation device 50 and severing system 51 in an expanded arrangement in which the first and second portions 54, 58 have been released from their respective capsules 60, 62. The first and second portions 54, 58 are configured to be self-expandable such that release from its respective capsule 60, 62 results in an automatic expansion of a greatest diameter of the first and second portions 54, 58. To achieve this effect, the first and second portions 54, 58 can be made of a shape memory metal mesh. Nitinol is one suitable material. In an alternate embodiment, the first and second portions 54, 58 can each include a collapsing hoop mechanism with support struts. In yet another embodiment, the first and second portions 54, 58 each comprise a series of triangular faces that collapse in the delivery position within the respective capsule 60, 62 against a bias and will expand upon being unsheathed form the respective capsule 60, 62. In yet another alternate embodiment, the first and second portions 54, 58 can each include a pivot and lock mechanism.

Figure 4A:
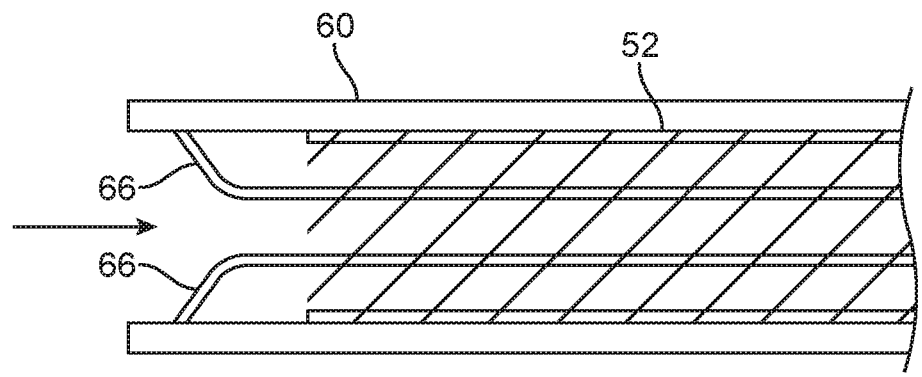
FIGS. 4A-4B are partial, enlarged, cross-sectional view of push/pull wires provided to actuate a distal capsule.
Figure 4B:
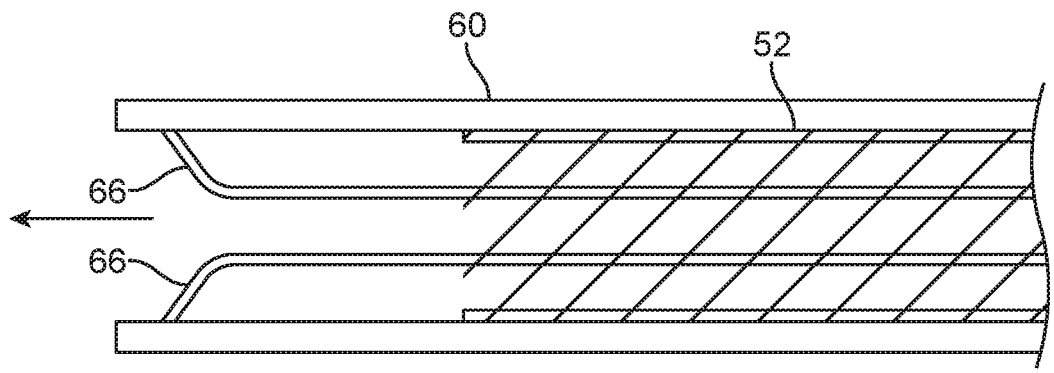
Figure 5:
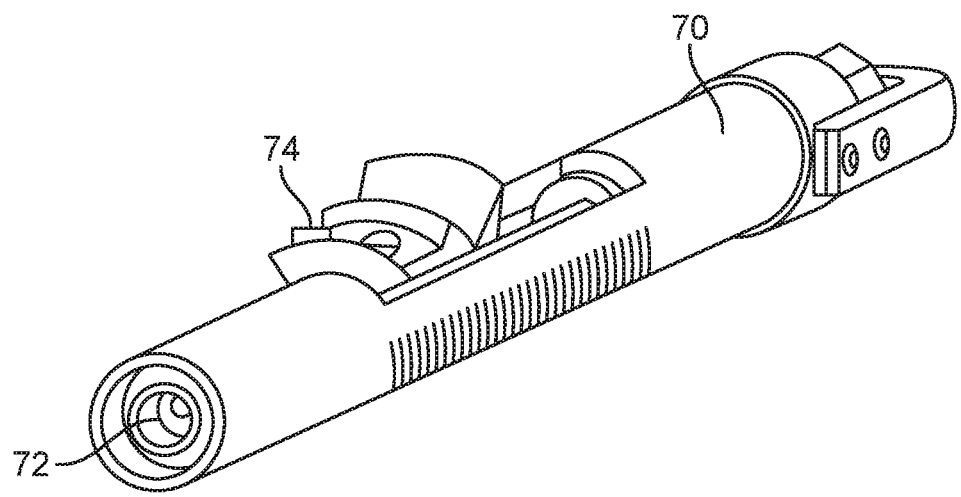
FIG. 5 is a perspective view of a handle assembly that can be used to control movement of the catheters and/or the push/pull wire of the device of FIGS. 2-4B.
Figure 6:
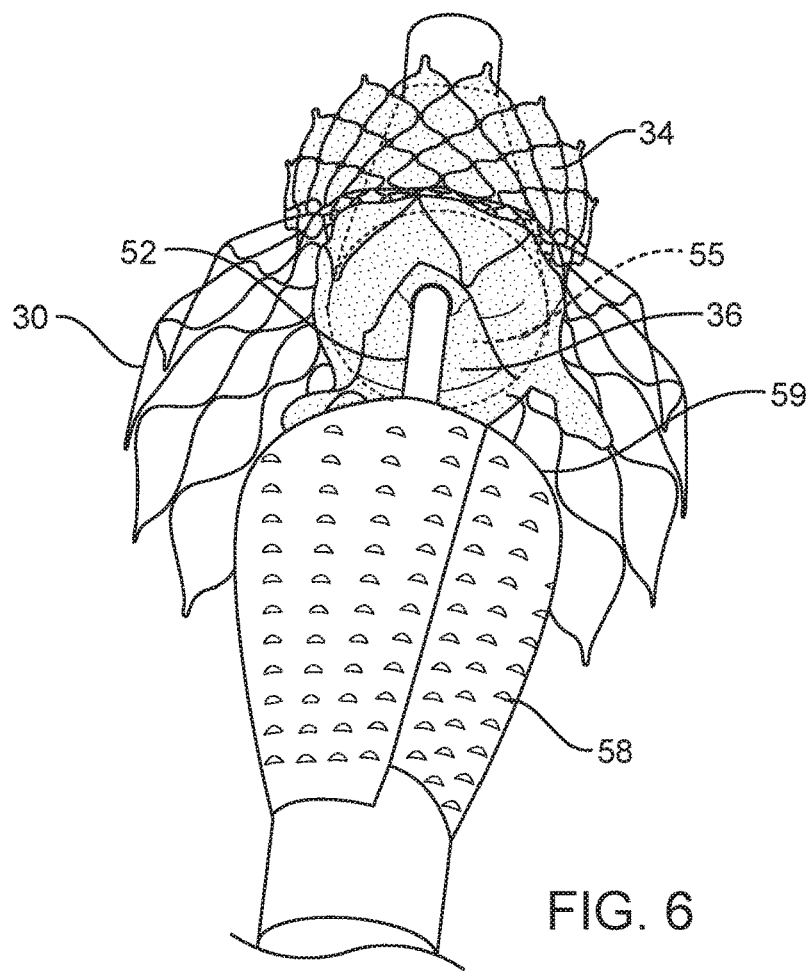
FIGS. 6-7 illustrate the first and second portions positioned on opposing sides of a valve structure of the prosthetic valve of FIGS. 1A-1B, in which the first and second portions can be brought in contact to sever leaflets of the valve structure.
Figure 7:
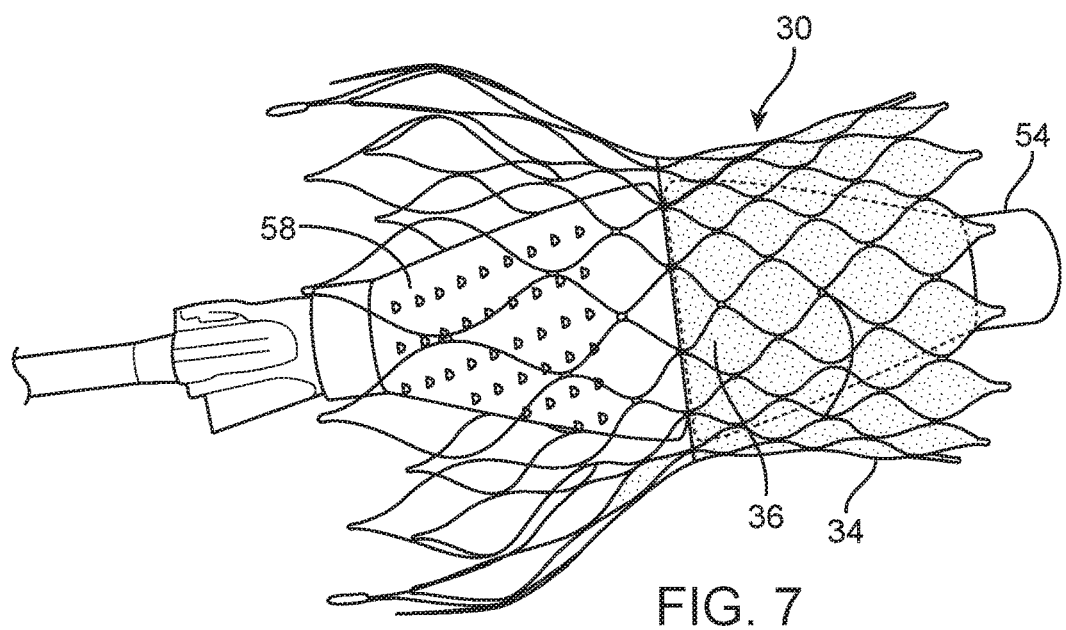
Figure 11A:
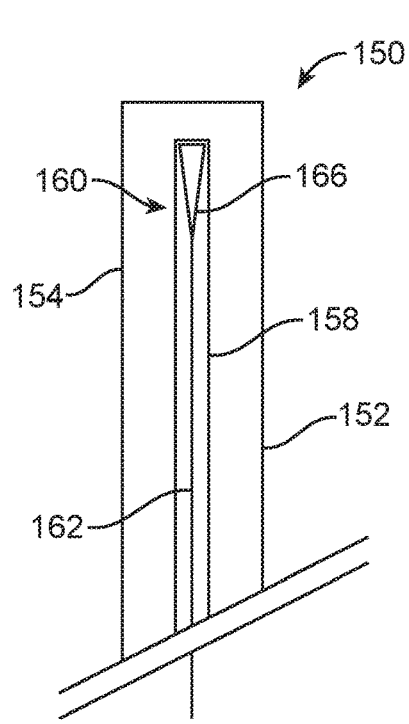
Figure 11B:
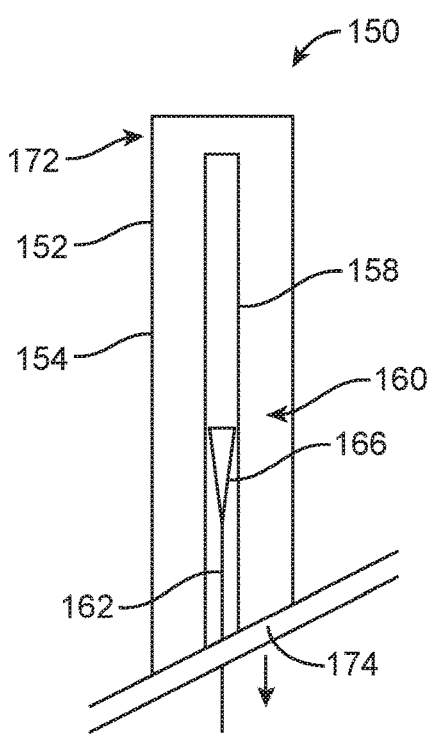
Figure 12A:
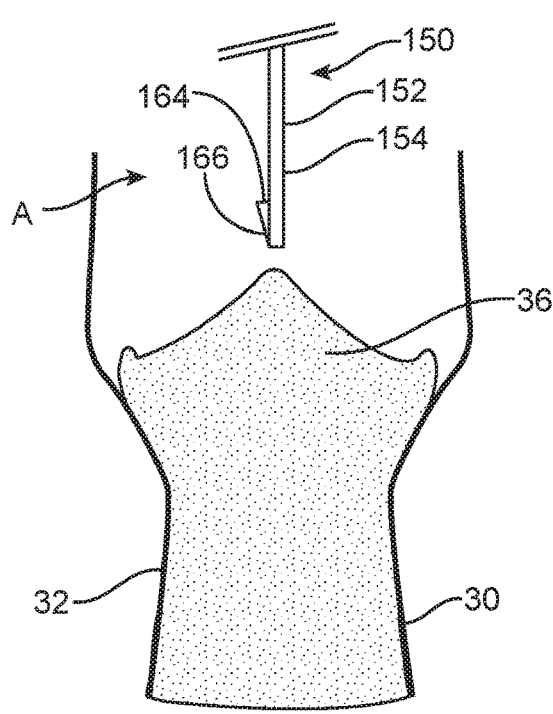
Figure 12B:
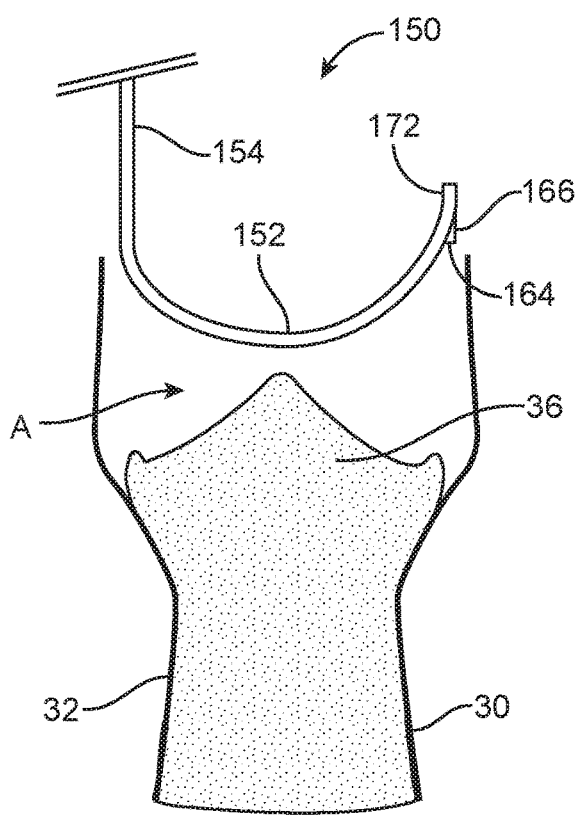
Figures 12C, 12D:
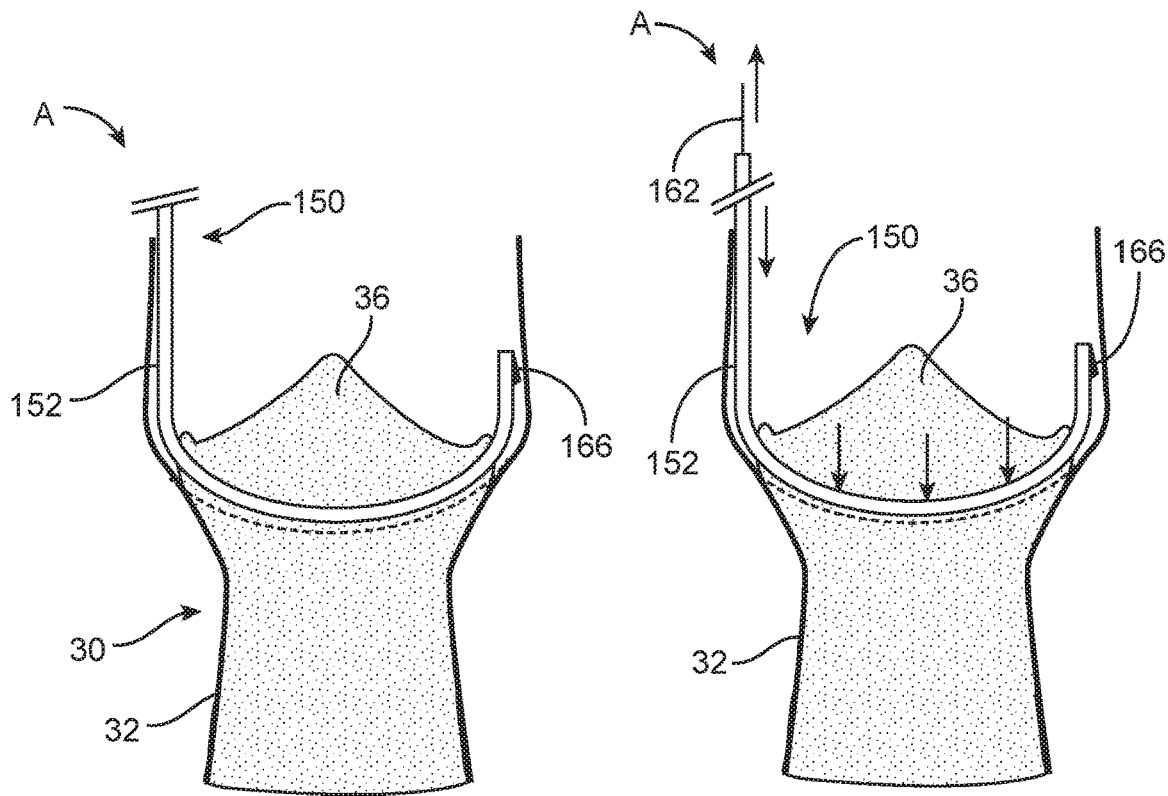
Figure 12E:
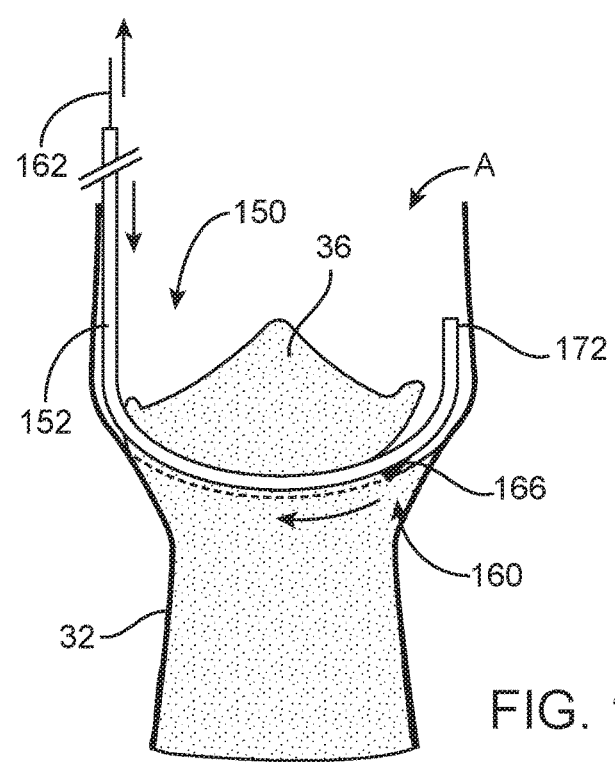

To retract the second capsule 62, the outer catheter 64 is proximally retracted. As shown in FIGS. 4A-4B, one or more push/pull wires 66 extend through respective lumens in the inner catheter 52 and connect to the first capsule 60 to actuate movement of the first capsule 60 to sheathe and unsheathe the first portion 54. Movement of the inner catheter 52, middle catheter 56, outer catheter 64, and push/pull wires 66 can be optionally accomplished with a handle assembly 70. One non-limiting example of a handle assembly 70 is illustrated in FIG. 5. The handle assembly 70 includes a connection end 72 in which each component 52, 56, 64, 66 can be operatively connected. The handle assembly 70 further includes one or more respective actuators 74 to individually or collectively control proximal/distal movement of the components 52, 56, 64, 66. It will be understood in view of this disclosure that only a select portion of the inner catheter 52, middle catheter 56, outer catheter 64 and push/pull wires 66 are shown and that these components can extend as far as needed to enable transcatheter delivery of the first and second portions 54, 58 to a valve while allowing the handle assembly 70 to remain exterior to the patient for use by a clinician.

The first and second portions 54, 58 are further configured to cooperatively sever one or more leaflets 34 at a time. This may be accomplished in a variety of ways. In one such embodiment, the first and second portions 54, 58 include a face or edge 55, 59 collectively forming a punch and die configuration (see FIGS. 3A-3B) such that when the first and second portions 54, 58 are in their expanded arrangement and are brought together on opposing sides of one or more leaflets 34 (FIGS. 6-7), the punch and die features collectively sever the leaflet(s) 34 to separate the leaflet 34 from a remainder of the prosthetic valve 30. Alternate embodiments can include a perforated edge 55. In other embodiments, the first and second portions 54, 58 can include electrodes on faces 55, 59, actuatable via the handle assembly 70, for example, which can be actuated to sever leaflet tissue upon contact.

To collect and protect a patient from debris created during the severance of leaflets of a valve and also to remove the severed leaflet(s), the embodiments disclosed herein can be used in combination with any known embolic protection devices. Example of such embolic protection devices include, but are not limited to, Sentinel Cerebral Protection System (CPS) available from Claret Medical of Santa Rosa, California, Embrella® and Embol-X® devices available form Edwards Lifesciences of Irvine, California. In various embodiments, the second portion 58 can also be configured to function as an embolic protection/removal and leaflet removal device. Once the leaflets are cut away and removed via the embolic protection device, a subsequent transcatheter aortic valve delivery and implantation procedure can be conducted in which a replacement valve is delivered and deployed in any known manner within the previously implanted stent frame. In one non-limiting illustrative example, the replacement valve is of the type disclosed with respect to FIGS. 1A-1B.

An alternate valve preparation device 150 is collectively illustrated in FIGS. 8A-12. The valve preparation device 150 includes a catheter 152 including a body 154 defining a plurality of lumens 156a, 156b. The first lumen 156a extends along length of the body 154 is open to a track 158 formed in the body 154, which extends radially from the first lumen 156a. Collectively, the first lumen 156a and the track 158 maintain a severing system 160 that includes a wire 162 supporting a blade 164 and a hook 166 (the blade 164 is only labeled in some figures for ease of illustration). The hook 166 can optionally correspond to the shape of the first lumen 156a as is best shown in FIG. 9. Optionally, as is shown in FIGS. 8A-8B, a cover 176 can be affixed at a distal end 172 of the body 154 to cover the hook 166 and blade 164 during delivery of the valve preparation device 150 (the cover 176 is shown in FIGS. 8A-8B as transparent for ease of illustration and is omitted in later figures). The wire 162 extends proximally to a handle assembly or the like (see the handle assembly 70 of FIG. 5, for example) that can be configured to actuate distal and proximal movement of the wire 162 and, thus, the blade 164 and hook 166 along the track 158. Provided in the second lumen 156b is an articulation device 170, which is configured to allow the catheter 152 to articulate. Optionally, the catheter 152 could be pre-shaped, such as a J shape, to preferentially seat within a valve leaflet. It could be straightened for insertion by following a guidewire, for example. In other embodiments, the blade 164 could be replaced with another cutting mechanism such as a radio-frequency (RF) cutting element, an ultrasonic cutting element, a plasma cutting element, a laser cutting element or an electrode cutting element, for example. The articulation device 170 can be of any known articulation devices (e.g., pull wire devices) that are known for providing articulation capabilities in catheters.

During use, the valve preparation device 150 is inserted, via transcatheter procedure, from the ascending aorta in a generally straight fashion in FIG. 8A. When the catheter 152 is proximate the aortic valve A, the catheter 152 is articulated to form a curved shape via the articulation device 170 to the position of FIGS. 8 and 12B and the catheter 152 is pushed against a base of one leaflet 36 on the ascending aorta side. In alternate embodiments described above, the catheter 152 is straightened with a guidewire for delivery proximate the aortic valve A and then transitions to the curved shape upon removal of the guidewire. To maintain the position of the catheter 152, generally constant and consistent pressure is applied to the device 150 by a clinician to ensure that adequate contact is made between the base of the leaflet 36 and the distal end 172 of the device 150. Optionally, the distal end 172 can include a tip 174 having a textured surface, barbs, or an adhesive to prevent the device 150 from slipping off the base of the leaflet 36. Once the distal end 172 of the device is in contact with the base of the leaflet 36, the hook 166 can engage the adjacent commissure joint 46 and find purchase there (indicated by the bold arrow and C in FIG. 13). In embodiments where the cover 176 is provided, the hook 166 may need to be drawn out of the cover 176 with the wire 162 before it will engage the adjacent commissure joint 46. The wire 162 is then pulled proximally via the handle assembly 70 (FIG. 5) or the like so that the blade 164 will correspondingly be pulled along the base of the leaflet 36 and thereby cut the leaflet 36 away from the stent frame 32 or valve skirt (or tissue of the valve if the valve is a native valve). It is noted that in FIGS. 12D-12G, a proximal portion of the catheter 152 is omitted so that the wire 162 is visible. The process of positioning the device 150 and severing one leaflet 36 is repeated until each desired leaflet 36 is substantially cut away and detached from the stent frame 32 or skirt. Alternately, the blade 164 can be used to form one or more slits without severing the leaflet 36. An embolic protection device (not shown) can be used in conjunction with the device 150 to account for any debris that may be created by the procedure. In addition, the embolic protection device can serve to capture and remove the leaflets 36, once detached. Examples of suitable embolic protection devices include, but are not limited to those listed above. Once the leaflets 36 are cut away and removed via the embolic protection device, a subsequent transcatheter aortic valve delivery and implantation procedure can be conducted in which a replacement valve is delivered and deployed in any known manner within the previously implanted stent frame. In one non-limiting illustrative example, the replacement valve is of the type disclosed with respect to FIGS. 1A-1B. It will be understood that the above-described valve preparation device 150 and related methods can alternatively be used on a native in valve in preparation for delivery and implantation of a prosthetic valve.

Yet a further valve preparation device 250 is illustrated in FIGS. 14A-14C and 16A-16C. The valve preparation device 250 includes a severing system 254. The severing system 254 includes a wire 256 and at least one arm 258 (e.g., two arms), each having an electrode 260. The arms 258 can be of a wire form or a ribbon form having two ends; wherein at least one end is fixed to the wire 256 via a cap 257 or the like. A distalmost end of each arm 258 can be connected either to the wire 256 (e.g., via one cap 257) or to the distal tip 264. Ribbon form material is beneficial in that it provides for a flat outer surface on which the electrode 260 can contact the leaflet 36. Each arm 258 is made of a shape memory material such as Nitinol, spring steel, polymeric shape memory materials, or wound spring constructions and is configured to be biased to the position of FIG. 14B. The illustrated embodiment includes two arms 258, however, more or fewer arms are envisioned in alternate embodiments. To collapse the arms 258 for transcatheter delivery, the device 250 includes a catheter or sheath 262 that can be slidably positioned over the arms 258. At a distal tip 264 of the device 250 includes an electrode 266 that is configured to pierce a leaflet 36 upon contact and energizing of the electrode 266. It is envisioned that the geometry of the distal tip 264 can comprise several shapes. The distal tip 264 is configured to supply enough energy to puncture the leaflet 36 but also must be configured to guide the device 250 into position. In the illustrated embodiment, the distal tip 264 is generally conical. Other envisioned shapes include a blunt, rounded or hourglass shaped tip, for example.

Figure 15:
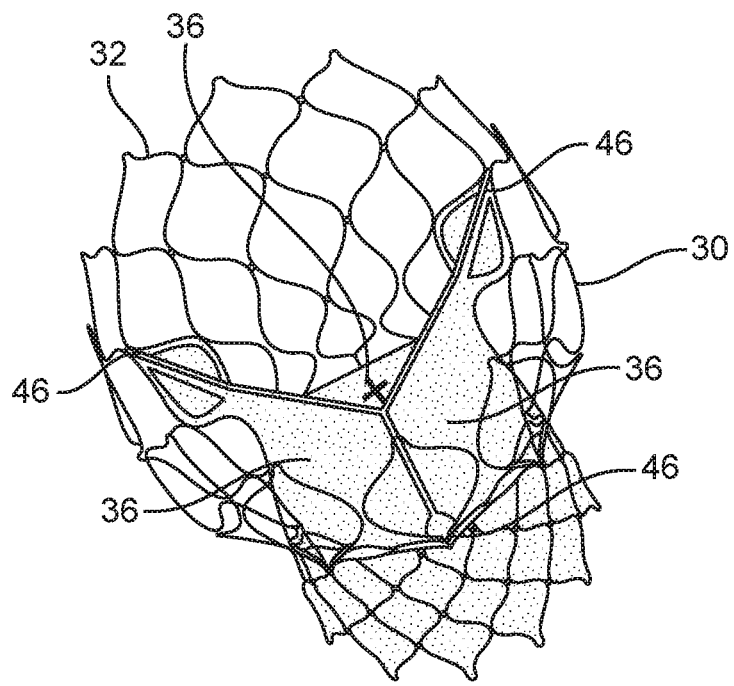
FIG. 15 is a perspective view of the prosthetic valve of FIGS. 1A-1B illustrating a target placement (X) at a base of a leaflet at which to direct a distal tip of the valve preparation device for removal of the leaflet.
Figure 16A:
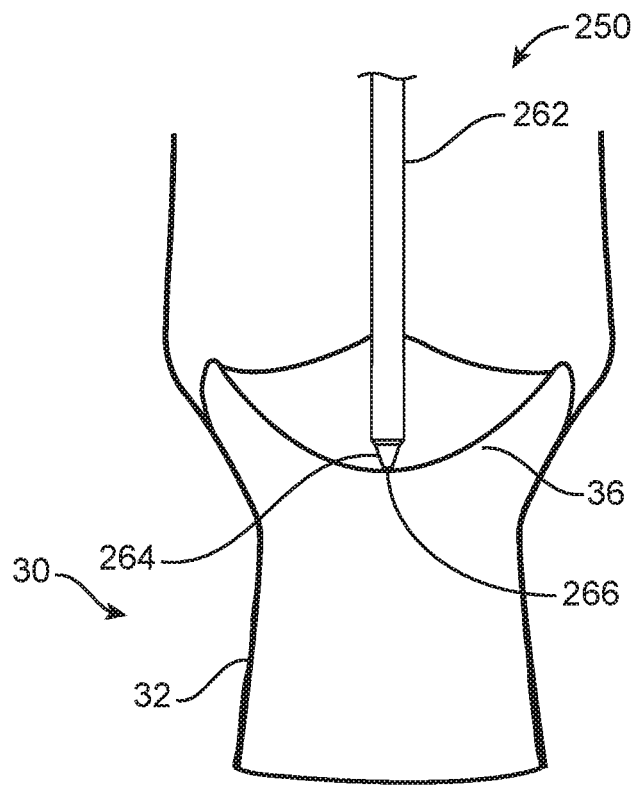
FIG. 16A, is a partial, schematic illustration of the valve preparation device of FIGS. 14A-14C being directed to the target placement (X) indicated in FIG. 15 (wherein a portion of the stent frame is removed for ease of illustration).
Figure 16B:
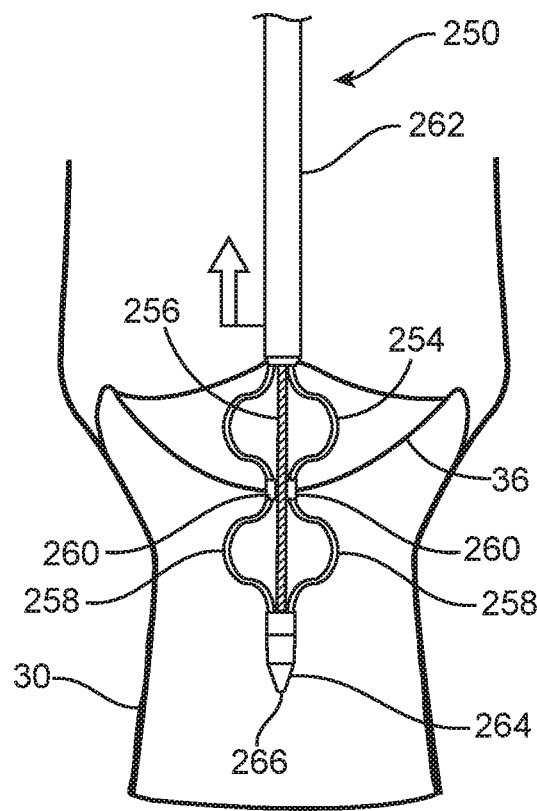
FIG. 16B is a partial, schematic illustration of the valve preparation device of FIGS. 14A-14C inserted through the leaflet.
Figure 16C:
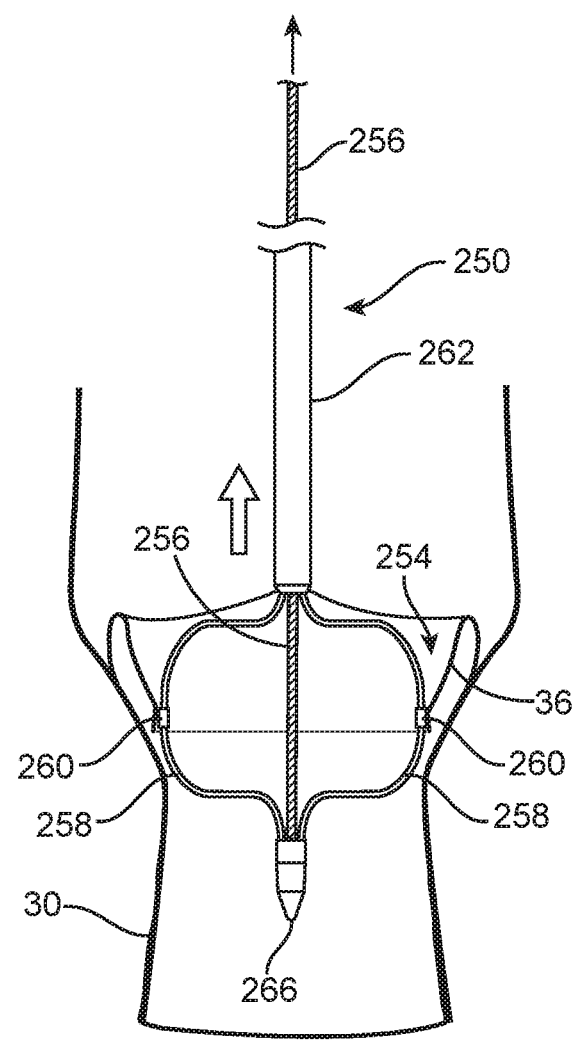
FIG. 16C is a partial, schematic illustration of the valve preparation device of FIGS. 14A-14C in which an electrode on each arm is activated to sever the leaflet and allow the arms to expand.
Figure 19A:
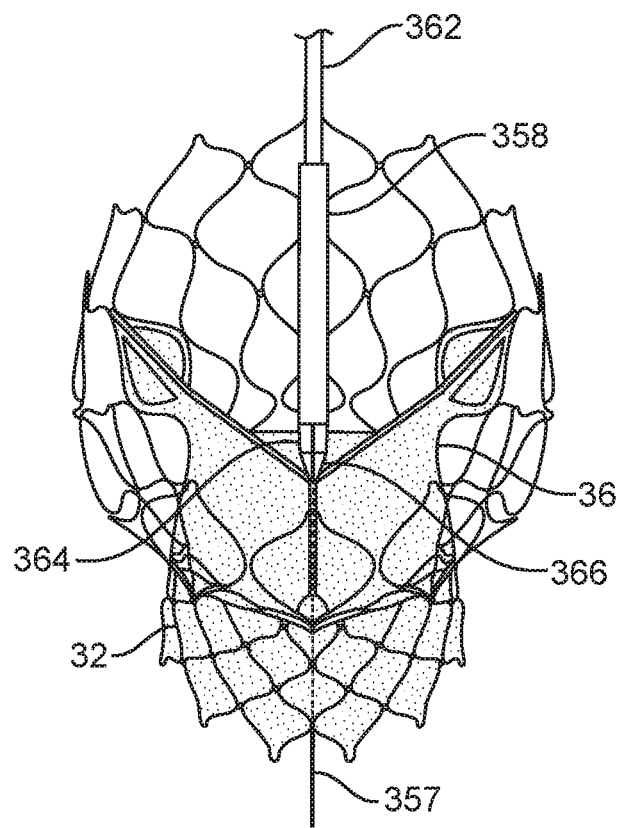
FIG. 19A is a schematic side view of the valve preparation device of FIG. 17 in the delivery arrangement and positioned at a leaflet to puncture the leaflet (wherein a portion of the stent frame is removed for ease of illustration).
Figure 19B:
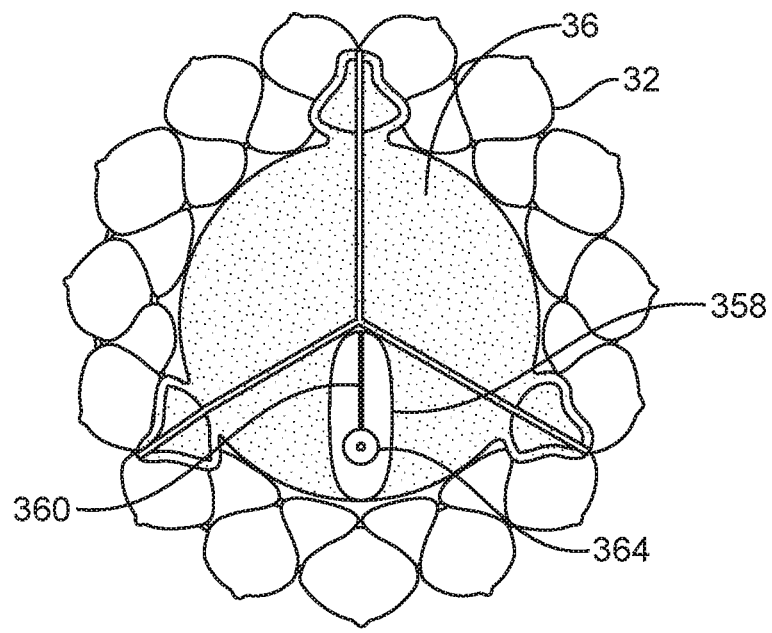
FIG. 19B is a schematic top view of the valve preparation device of FIG. 17 in the deployed arrangement, creating a slit in one leaflet.

In one example method, operation of the valve preparation device 250 is conducted as follows. In a delivery configuration, the device 250 is provided with the sheath 262 covering the arms 258 so that the arms 258 are collapsed within the sheath 262 such that the device 250 has a first width or profile. The device 250 is delivered in the delivery position (FIG. 16A) to the base of one leaflet 36 such that the distal tip 264 touches the leaflet 36 (the base is indicated by X in FIG. 15). The electrode 266 is activated to lacerate the base of the leaflet 36 and form an opening through which the device 250 can be positioned. Once the device 250 is positioned within the leaflet 36 such that the severing electrodes 260 are generally adjacent the leaflet 36, the distal tip 264 is retracted into the sheath 262 so that the arms 258 naturally bow outwardly to contact the leaflet 36 as is generally illustrated in FIG. 16B. As can be seen, the leaflet 36 will constrict and prevent full expansion of the arms 258 into their natural position at this stage. Upon activating the electrodes 260, the electrodes 260 will sever the leaflet 36 and allow the arms 258 to more fully expand to their natural position as the leaflet 36 is severed. To further direct the electrodes 260 for cutting, the wire 256 is drawn proximally to further direct the electrodes 260 to move laterally to further engage the leaflet 36. Although FIG. 16C generally illustrates the electrodes 260 moving in a horizontal direction, horizontal movement may be insufficient to effectively ablate leaflet 36 tissue when the electrode 260 approaches a commissure joint 46. Therefore, the electrodes 260 of various embodiments are configured to cut both horizontally and vertically via manipulation of the sheath 262 and the wire 256. In one embodiment, the wire 256 can extend proximally from the distal tip 264 to a handle assembly (not shown, see FIGS. 1A-1B and related disclosure provided as one suitable example) of the device 250, in which the actuator 74 of the handle assembly 70 (FIG. 5) controls tension in the wire 256 and, therefore, control proximal and distal movement of the wire 256 with respect to the sheath 262 and the handle assembly 70.

Severing the leaflet 36 is most effectively accomplished when the arm electrodes 260 move laterally while following the curvature of the leaflet 36 up to the commissure joint 46. Collapsing the arms 258 with the wire 256 will laterally direct the electrodes 260 while manually retracting the device 250 will supply adequate elevation. During this step, the sheath 262 is maintained in the retracted position of FIG. 16C in part to anchor the arms 258 and their respective electrodes 260 in position. Once the leaflet 36 is sufficiently lacerated (i.e. separated from the stent frame 32 or skirt), the arms 258 are drawn back into the sheath 262 into the delivery position of FIG. 16A and then the device 250 can be moved to another leaflet 36, as desired, and the leaflet severing process can be repeated. Once each desired leaflet is severed, the device 250 is retracted from the patient the same way the device was delivered. The severed leaflets 36 are captured in a provided embolic protection device of the types disclosed above and then are subsequently removed along with the embolic protection device. As with the prior embodiments, once the leaflets 36 are cut away and removed via the embolic protection device, a subsequent transcatheter aortic valve delivery and implantation procedure can be conducted in which a replacement valve is delivered and deployed in any known manner within the previously implanted stent frame. In one non-limiting illustrative example, the replacement valve is of the type disclosed with respect to FIGS. 1A-1B.

It will be apparent from the present disclosure that the valve preparation device 250 can also be used to cut a slit in the leaflet from the margin of attachment (MOA) near the area where the leaflet meets the frame to the free edge of the leaflet (the area of the leaflet closest to the center of the aortic annulus). This method does not remove any portion of the leaflet, the method simply places a slit in the leaflet to allow the leaflet to open when a second prosthetic valve is implanted in the patient to allow flow of blood to the coronary arteries which may have otherwise been blocked by the initial leaflet being pinned between the frame of the first and second implants.

In one example method, the device 250 includes one arm 258 and penetrates the leaflet 36 in the same manner described above with respect to FIG. 16A. After penetration of the leaflet 36, the device 250 would have one arm 258 that would expand from the margin of attachment toward the free edge of the leaflet 36 with radio frequency (RF) energy being applied to the electrode 260. The biasing force of the shape memory biased arm 258 trying to expand and the RF energy from the electrode 260 can slice or sever the leaflet 36 allowing the leaflet 36 to open with a "V" shaped slot allowing the flow of blood into the coronaries. The arm 258 would be aligned approximately 90 degrees from what is shown in the FIG. 16C. In another embodiment, the one arm 258 could expand along the margin of attachment from the point of leaflet penetration up to the commissure. The result would be a leaflet that would not be severed but would be slit and could fold over or otherwise provide coronary access/perfusion as the second valve is deployed.

Referring now in addition to FIGS. 17-19B, which illustrate another embodiment of a valve preparation device 350.

Figure 14A:
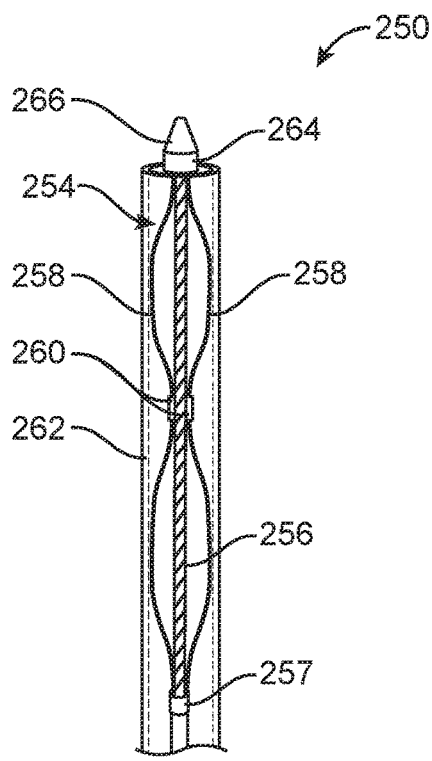
FIG. 14A is a partial, schematic illustration of an alternate valve preparation device including a severing system covered by a sheath (the sheath is shown as transparent for ease of illustration).
Figure 14B:
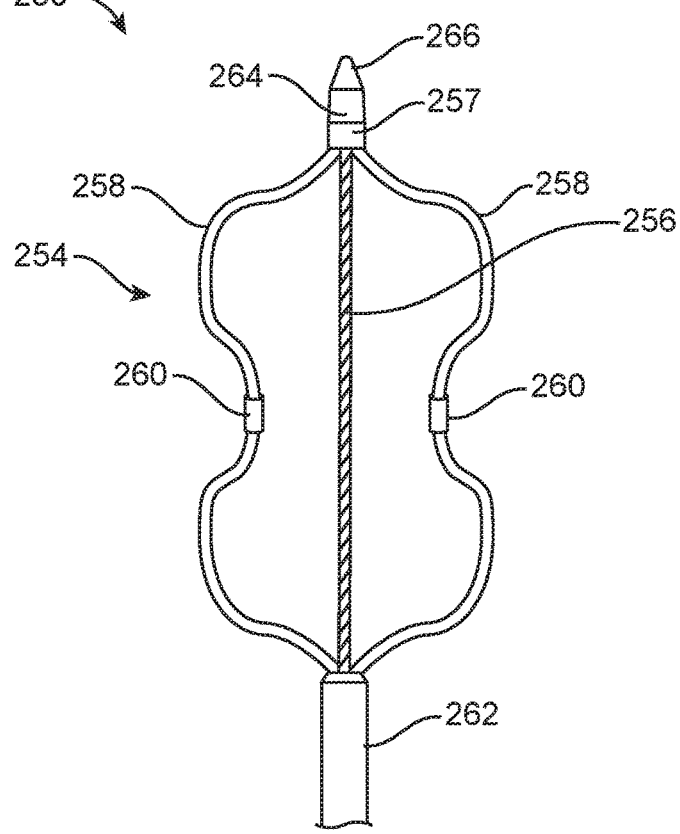
FIG. 14B is a partial, schematic illustration of the valve preparation device of FIG. 14A showing the sheath retracted to expose the severing system.
Figure 14C:
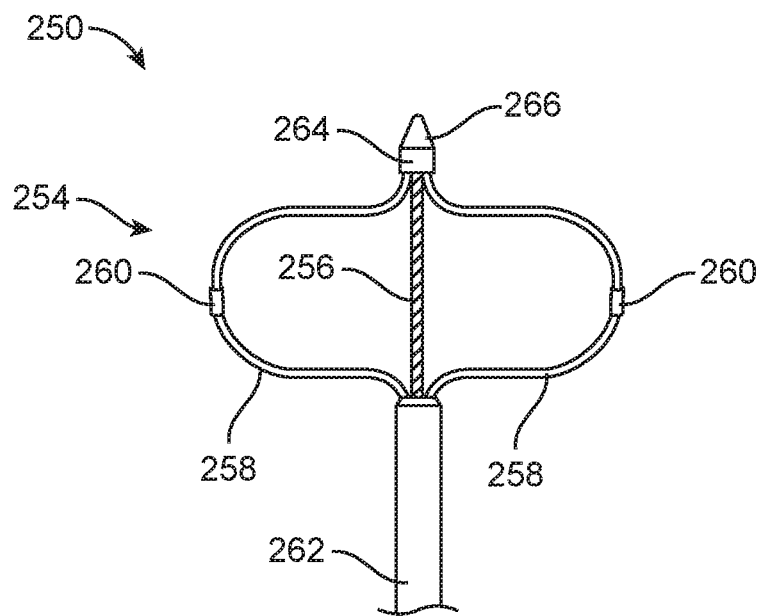
FIG. 14C is a partial, schematic illustration of the valve preparation device of FIGS. 14A-14B illustrating a tip being retracted into the sheath to force arms of the severing device outwardly.

The valve preparation device 350 is largely similar to that of FIGS. 14A-14C except that arms 258 are substituted with a balloon 358. The balloon includes an outer surface on which an elongated, wire-form electrode 360 is positioned and extends from a tip 364 to a delivery catheter 362. As with prior disclosed embodiments, the tip 364 can be configured to puncture a leaflet 36, and can include an electrode 366, for example. The device 350 can further include a guidewire lumen within support 356a/tip 364 and which extends through the device 350 for receiving a guidewire 357. The device 350 can also include an inflation lumen 356b for controlling the inflation of the balloon 358 via saline without or without contrast dye, for example. As will be understood, the valve preparation device 350 can include a handle, such as that of FIG. 5. The handle can, for example be connected to an inflation source (not shown) and can include one or more actuators for controlling the electrode 360.

In one example method, the device 350 penetrates the leaflet 36 in the same manner described above with respect to FIG. 16A. After penetration of the leaflet 36, the balloon 358 is inflated while energizing the electrode 360 to cut the leaflet 36. The biasing force of the balloon 358 trying to expand and the radio frequency (RF) energy from the electrode 360 can slice or sever the leaflet 36 allowing the leaflet 36 to open with a "V" shaped slot allowing the flow of blood into the coronaries (see, in particular, FIGS. 18A-19B). The electrode 360 can be aligned via imaging to direct the cut through the center of the leaflet 36, or preferentially to one side or the other if so desired. The device 350 can alternatively been configured to include multiple longitudinal electrodes 360. Each electrode 360 could be configured to be fired simultaneously or in sequence, as desired.

In view of the present disclosure, it will be understood that 100% of the leaflets 34 may not necessarily be removed from the stent frame, skirt, or other remaining portions of the prosthetic valve. As used herein, removing, severing and cutting the leaflet from the remainder of the valve shall be understood to indicate that substantially all of the leaflet has been separated from the stent frame, skirt, or other remaining portions of the prosthetic valve so that any remaining leaflet proximate the margin of attachment does not present a risk of blood flow blockage after a replacement prosthetic valve is implanted adjacent the leaflet. It will be understood that temporary valves may need to be provided to provide hemodynamic stability when leaflets are removed.

Although the present disclosure has been described with reference to preferred embodiments, workers skilled in the art will recognize that changes can be made in form and detail without departing from the spirit and scope of the present disclosure.

What is claimed is:

1. A valve preparation device comprising:
 a severing apparatus including a wire and a first arm that is biased to bow outwardly with respect to the wire; the first arm including a distal section, a proximal section, and a first electrode at an electrode section of the first arm, the electrode section positioned between the distal section and the proximal section;
 a conically shaped tip connected to a distal end of the wire wherein the conically shaped tip includes a piercing electrode, and the valve preparation device is configured to energize the piercing electrode to form an opening through a heart valve leaflet; and
 a sheath slidably movable from a delivery position in which the sheath covers the severing apparatus and a deployed position in which the sheath is proximally retracted to uncover the severing apparatus; wherein, in the deployed position, the first arm is configured to move from a first orientation to a second orientation, a portion of the distal section and a portion of the proximal section each extend a distance farther from the wire as compared to a distance the first electrode extends from the wire in the first orientation, and the portion of the distal section and the portion of the proximal section each extend a distance closer to the wire as compared to a distance the first electrode extends from the wire in the second orientation; and the valve preparation device is configured to energize the first electrode to cut through a thickness of the heart valve leaflet while moving the first arm from the first orientation to the second orientation.

2. The valve preparation device of claim 1, wherein the severing apparatus further includes a second arm comprising a second electrode.

3. The valve preparation device of claim 1, wherein the first arm is one of a plurality of arms and the piercing electrode interconnects the plurality of arms.

4. The valve preparation device of claim 1, wherein the first arm comprises ribbon wire.

5. The valve preparation device of claim 1, wherein the wire is coaxially positioned with respect to the sheath.

6. The valve preparation device of claim 1, further comprising a handle assembly, wherein the wire extends proximally from the conically shaped tip to the handle assembly.

7. The valve preparation device of claim 1, wherein the conically shaped tip is connected to the distal end of the wire with a cap.

8. The valve preparation device of claim 1, wherein a distal end of the first arm is connected to the distal end of the wire.

9. The valve preparation device of claim 1, wherein the first arm comprises a flat surface.

10. The valve preparation device of claim 1, wherein the first arm is made of a shape memory material.

11. The valve preparation device of claim 1, wherein, in the deployed position, proximal drawing of the wire is configured to bow the first arm outwardly with respect to the wire.

12. The valve preparation device of claim 1, further comprising a handle assembly including an actuator coupled to a proximal end of the wire, wherein the actuator controls the proximal and distal movement of the wire relative to the sheath and handle assembly.

13. The valve preparation device of claim 1, wherein the first electrode comprises a length that is less than a length of the electrode section.

14. The valve preparation device of claim 1, wherein, in the first orientation, the electrode section is outwardly concave from the wire.

15. The valve preparation device of claim 1, wherein, in the first orientation, the first electrode is positioned at a location of the electrode section that is closest to the wire.

16. The valve preparation device of claim 1, wherein, in the second orientation, the electrode section is outwardly convex from the wire.

17. The valve preparation device of claim 1, wherein, in the second orientation, the first electrode is positioned at the location of the electrode section that is farthest away from the wire.

* * * * *